United States Patent [19]
Sung

[11] 3,945,076
[45] Mar. 23, 1976

[54] CIRCULAR TOOTHBRUSH

[76] Inventor: Thomas Sung, 217 Park Row, New York, N.Y. 10038

[22] Filed: Dec. 10, 1974

[21] Appl. No.: 531,312

[52] U.S. Cl. ..................... 15/21 R; 128/46; 310/80
[51] Int. Cl.² ........................................ A46B 13/02
[58] Field of Search ............... 15/22 R, 22 C, 98 R; 310/80, 82; 128/45, 46; 74/86

[56] References Cited
UNITED STATES PATENTS

| | | | |
|---|---|---|---|
| 795,213 | 7/1905 | Fitz | 15/22 R UX |
| 807,299 | 12/1905 | Marshall | 15/22 R UX |
| 816,506 | 3/1906 | Shelton | 310/80 X |
| 873,123 | 12/1907 | Gardy | 15/22 R UX |
| 1,102,885 | 7/1914 | Dorment | 128/45 |
| 2,439,262 | 4/1948 | Nalbach et al. | 15/22 R X |
| 3,046,584 | 7/1962 | Wepfer | 15/22 R |
| 3,104,405 | 9/1963 | Perrinjaquet | 15/22 R |
| 3,133,297 | 5/1964 | Gerber et al. | 15/22 R |
| 3,702,487 | 11/1972 | Sung | 15/22 R |

*Primary Examiner*—Edward L. Roberts
*Attorney, Agent, or Firm*—Lowe, King, Price & Markva

[57] ABSTRACT

A circularly movable mechanical toothbrush having a fly wheel type drive shaft loosely joined to a rod near one edge thereof. Actuation of the fly wheel causes the rod to rotate in a distinct motion that causes toothbrush bristles to be maintained at all times toward selected teeth, which motion compactingly massages gums during a gradual approach stroke, aligns the bristles with tooth striations and interdental spaces during a sweeping brush stroke, and keeps the bristles disposed away from the user's cheek during a return stroke.

6 Claims, 5 Drawing Figures

CIRCULAR TOOTHBRUSH

FIELD OF THE INVENTION

This invention relates to mechanical toothbrushes for personal use and in particular relates to circularly movable electric toothbrushes which are selectively reversible.

BACKGROUND OF THE INVENTION

Review of the Prior Art

Many attempts have been made in the prior art to provide a mechanically operated toothbrush for personal use, most being electrically driven. In U.S. Pat. No. 2,598,275, Lakim discloses an electrically actuated oscillatory toothbrush having a reciprocable shaft driven by an oscillatory or vibratory motor. In U.S. Pat. No. 2,655,674, for example, Grover provides a lip guard and a pair of rotary brushes for cleaning both sides of a row of teeth simultaneously. In my prior U.S. Pat. No. 3,702,487, there is described a mechanical toothbrush having a crank-shaped drive shaft that maintains the bristles disposed at all times toward selected teeth. The present invention provides an alternative means of accomplishing the objectives of my prior patent.

These and other prior art attempts have shown keen awareness of the problems which a toothbrush user commonly encounters in brushing the multi-surfaced teeth and gums without tending to move the gums away from the necks of the teeth or to force food particles therebetween. However, except for my prior patent no known prior art device has effectively solved these problems and provided a mechanically operated toothbrush which cleans the sides of teeth, the cuspidate surfaces thereof, and the interdental areas while selectively able to massage gums as dexterously, efficiently, and sensitively as a hand-operated toothbrush is commonly able to do.

The apparent difficulty is that the sweeping motion generally used in hand operaton of a toothbrush is not effectively simulated by the rotary or reciprocatory motion of the prior art devices. Another difficulty of prior art devices is generally caused by unwanted contact of bristles of rotary toothbrushes with the cheek or gums. The device of the present invention has been found to be as efficient as the hand brushing method.

SUMMARY OF THE INVENTION

Accordingly, it is the object of this invention to provide a mechanically operated toothbrush which moves in a path of revolution to provide a sweeping motion during toothbrushing therewith by a personal user.

It is another object of this invention to orient the bristles of the toothbrush of this invention in a general toothward direction at all times which is generally deemed most beneficial in brushing teeth.

It is a further object of this invention to provide a gradual onset of contact of the bristles with the gums as the bristles approach the necks of the teeth, thereby imparting a compacting type of massage to the gums, and also to provide a means for cleaning crown areas by transverse sweeping thereover.

In satisfaction of the foregoing objects and advantages there is provided by this invention a mechanically driven toothbrush comprising:

A. a handle, comprising a housing which is adaptable for manual clasping, having sides, a top and a bottom, a rotary drive means mounted within said housing, and an externally mounted actuating means for reversibly operating the rotary drive means; B. a revolutionary reversible drive means comprising a drive shaft rigidly connected to the rotary drive means and to a fly wheel, an actuating rod loosely connected on the opposite side of the fly wheel in an off-center position; said actuating rod extending through the top of the housing and connected thereto but permitted to be rotated independently of the housing; and C. a toothbrush having a stem which is interchangeably attached to the upper portion of said actuating rod.

DESCRIPTION OF THE PREFERRED EMBODIMENT

The objectives of the invention are attained by using a handle of convenient shape and size within which is mounted a reversibly operable, rotary drive means, such as a fluid-operable drive means, as disclosed in U.S. Pat. No. 3,273,189 and Re 26, 589, a mechanical motor of spring-drive type, but preferably an electrical motor of conventional design having an armature and conventional field structure such as is disclosed in U.S. Pat. No. 3,274,631 and 3,160,902. The electric motor may be driven by AC current or by batteries of the popular recharging plug receptacle type.

The handle has top, bottom and conventional sides. On one side of the handle, which is suitably made of a tough but resilient plastic such as polypropylene, are switch means for starting and stopping the motor and for selectively reversing its direction of rotation.

Figure 1:
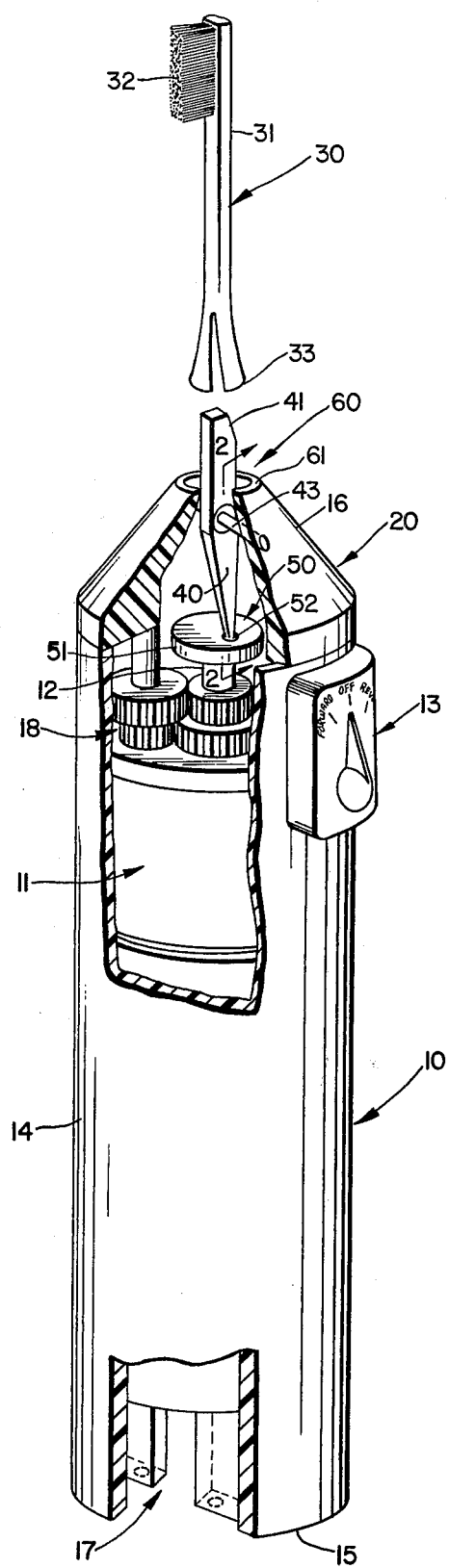
FIG. 1 is a side elevational view of the circularly operated electric toothbrush of this invention partially in section.

The circularly operated electric toothbrush of this invention comprising a handle 10, a sloped head 20, a revolutionary drive means in the form of fly-wheel drive shaft 50 for moving an actuating rod 40 along a path of revolution, and a toothbrush 30 which is interchangeably attached to rod 40, as shown in FIG. 1. The handle 10 comprises a housing, an electric motor 11 mounted therein with drive shaft 12, and switch means 13 for actuating the motor reversibly. The housing, which is adaptable for manual clasping, comprises the sides 14, the bottom 12 and top portion 16. The electric motor 11 may be driven by connection to an electrical outlet by a cord at 17 or the motor may be operated by batteries as is well known. Gear means 18 may be provided as desired and as well known to control the speed of drive shaft 12 by motor 11.

The interchangeable toothbrush 30 comprises the stem 31, the bristles 32, and interchangeable joint means 33. Any commercially available toothbrush 30 may be used as a part of the toothbrush of this invention. Joint means 33 may be of any well known form of construction so long as the toothbrush is removably attached.

An essential novelty of the device of this invention resides in the particular driving means involving use of the fly wheel means 50. In this device, fly wheel 50 is rigidly attached at its bottom center 51 to drive shaft 12 attached to the electric motor and revolves as the motor causes the drive shaft 12 to rotate. It is, of course, to be understood that the speed of rotation of the fly wheel 50 may be regulated or controlled by the use of the gear train 18 as is well known in the art. The fly wheel may, of course, also be an enlarged extension of drive shaft 12 and not merely an additional member. It is only mecessary that the rod 40 be offset from center to provide the pattern of revolution of the invention.

The fly wheel 50 is loosely connected on its opposite side in an off center position and preferably near an edge to an actuating rod 40. The actuating rod 40 is preferably attached to fly wheel 50 by a pin joint 52 or other suitable means so that the rod is permanently attached but retains at least some side to side and up and down movement. Thus, in pin joint 52, sufficient space is provided in the joint to allow the rod 40 to move vertically as necessary to assist in its movement at the head mount 60 as described hereinafter. The relationship of the fly wheel 50, drive shaft 12 and actuating rod 40 may be seen clearly in the views of FIGS. 1 and 2. Actuating rod 40 extends to and beyond head mount portion 60 to connect with the stem 33 of toothbrush 30.

From its connection with fly wheel 50, actuating rod 40 extends upwardly to head mount portion 60, preferably at a slight angle from vertical. The angle of the actuating rod is preferably about 70° to 80° and most preferably about 80° to 85°. The actuating rod extends to and beyond heat mount or joint portion 60 to a point 41 where it is removably attachable to the stem 33 of toothbrush 30. The toothbrush joint of stem 33 and upper portion 41 of rod 40 can be of any desired design so long as the actuating rod 40 and toothbrush handle are maintained in generally rigid but detachable relationship. The well-known snap-on type of connection suitable for attaching the toothbrush. For example, the actuating rod 40 at its upper portion may be provided with a receiving portion at 41 to receive the stem 33 of toothbrush 30. Snap-on connections of this type are well known in the toothbrush art and need not be further described here. For example, see my prior U.S. Pat. No. 3,702,487 where a connection of this type is disclosed.

As indicated, the actuating rod 40 extends to and beyond head mount portion 60 and at the head mount portion 60, connecting means are provided to attach rod 40 to the neck of portion 60 so that rod 40 is well supported and maintained in proper relationship with fly wheel 50 but still is allowed to rotate as fly wheel 50 turns. In one embodiment as shown in FIG. 1 and detailed in FIG. 2, a double countersink connection is utilized comprising countersink 42 and 42' and horizontal guide pin 43. In this embodiment, head mount portion 60 is provided with ring means 61 and rod 40 passes loosely therethrough. Guide pin 43 is rigidly connected at both ends to the top of head mount 60 and thus is maintained in rigid relationship therewith and passes loosely through a hole or opening 45 in the narrow portion 44 of rod 40. While the ends of pin 43 are maintained in rigid relationship with the housing, means must be provided for rod 40 to rotate as fly wheel 50 turns. According to this embodiment, rod 40 is countersunk at 42 and 42' to permit clearance of this portion of rod 40 over pin 43. The hole or opening 45 in the narrow portion 44 of rod 40 through which pin 43 passes is sufficiently large to permit pin 43 to pass loosely therethrough. Thus, when rod 40 is rotated by action of fly wheel 50, the opening in rod 40 is large enough to permit vertical movement of rod 40 as it rotates. This vertical movement is sufficient to permit the rod to move on pin 43 as the fly wheel 50 rotates, the rod also moving vertically at joint 52. Countersunk portions 42 and 42' prevent the remaining portions of rod 40 from hitting the pin 43 as rod 40 moves with the rotation of fly wheel 50. It should be understood that the deeper the countersink portions 42 and 42', the smaller can be opening 45 for pin 43. On the other hand, shallow countersink portions require larger openings for the pin.

Figures 2, 4:
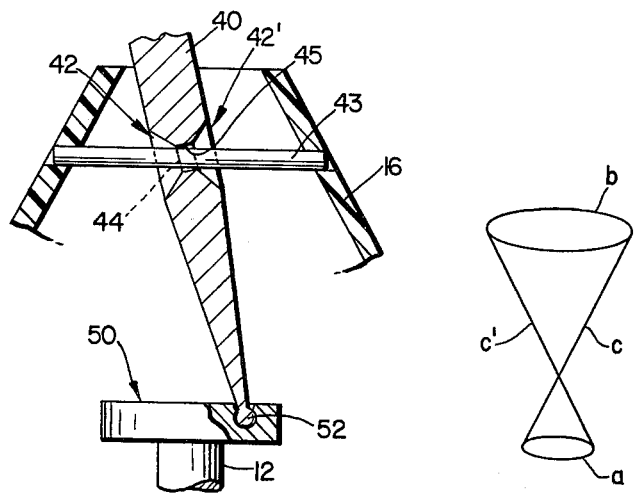
FIG. 2 is a sectional view taken in the direction of the arrows 2—2 in FIG. 1, showing details of the construction of the head mount.
FIG. 4 is a diagrammatic view showing the motion pattern made by the toothbrush of the invention.
Figure 3:
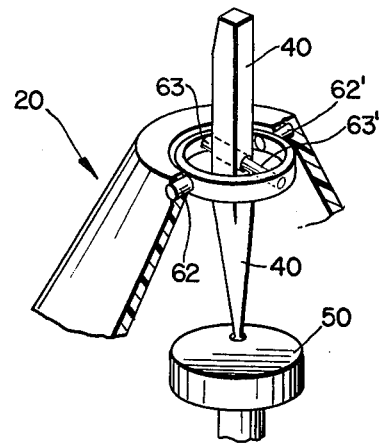
FIG. 3 is an alternative embodiment of the head mount.

While this is a preferred construction of maintaining alignment of rod 40, an alternative construction is shown in FIG. 3. In this construction, ring 61 is attached to head 60 with rod 40 passing therethrough. Ring 61 is attached to head 60 by opposite disposed horizontal pins 62 and 62' which maintain ring 61 in a generally horizontal relationship but still permit the ring to move vertically by movement around the axis of pins 62 and 62'. Rod 40 is loosely attached to ring 61 by pins 63 and 63' which pass from ring 61 to the rod 40. Pins 63 and 63' are located about 90° from each of pins 62 and 62' and are adapted to provide vertical movement of ring 61 with respect to rod 40 via pins 63 and 63'. The double vertical movement of ring 61 with respect to rod 40 by reason of the two sets of pins thus provides rotation of rod 40 within ring 61 somewhat like a universal joint. In the embodiments of FIGS. 2 and 3, the construction is such as to permit sufficient movement or "play" at head mount portion 60 to accommodate movement of rod 40 as fly wheel 50 rotates. It should be understood however that while the specific embodiments of FIGS. 2 and 3 are preferred for the head mounting of the rod, other constructions may also be employed.

These particular connections at head mount 60 are necessary to minimize wear at the point where actuating rod 40 exits head 20 as at this point the angled and turning rod will be subjected to its greatest wear during use. It will also be understood that this construction also provides a unique combination of vertical and circular motion and thus provides the novel action on the teeth and gums when in use.

As may be seen in the diagram of FIG. 4, rotation of the fly wheel 50 will form a circular pattern indicated by the letter a. The combination of the actuating rod 40 and toothbrush 30 forms a generally angular line as indicated by c and c'. Therefore, the pattern of movement of the bristles 32 of toothbrush 30 will be generally as indicated by line b in FIG. 4, which pattern of movement provides the unique cleaning action of the toothbrush of this invention.

Figure 5:
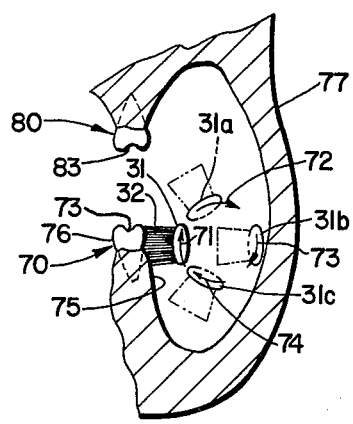
FIG. 5 is a front-elevation sectional view of the left side of a user's mouth in which the toothbrush stem moves in the direction of the arrows 71, 72, 73 and 74 in FIG. 1.

Referring now to FIG. 5, where one of the possible of the revolving brush against the teeth is shown as limited by the degree of movement provided by the head mount portion, when the brush stem 31 revolves away from the solid position shown, it moves along the direction 71 so that the bristles 32 penetrate deeply into interdental areas and sweep food particles away. When the stem 31 is in the reverse position 31a, it continues moving along the direction 72. When the stem 31 is in the return position 31b, it moves along the direction 74.

Each of the directions 71, 72, 73 and 74 of FIG. 5 are arcs of a circle limited as indicated above. The bristles 32 of the toothbrush 30, however, maintain alignment at all times and consequently describe an arc because of their width, radius being determined by the angle of the rod 40 while the orientation of the bristles 32 is determined by the diameter of the fly wheel 50.

When a user is operating the toothbrush of this invention with one hand, he is able to direct its operation so that the preferred dental techniques of brushing away from the gums and toward the teeth is readily used. The bristles 32 are able to penetrate between adjacent teeth and are able to follow the striations of the teeth. By bringing the lower and upper teeth 70 and 80, respectively, fairly close together, the bristles 32 compactingly massage the gums 75 of the lower jaw when passing by in the approach position 31c, vigorously brush the necks 76 of the lower teeth 70 when in the brush position, and outwardly sweep over the crowns 83 of the upper teeth 80 when in the reverse position 31a. Subsequently, when executing the circular return operation as shown in return position 31b, the back of the stem 31 moves lightly downward against cheek 77 without any contact of the bristles 32 therewith.

A simple twist of the user's wrist, after selectively reversing the motor by touching the reversible actuating means therefor, is sufficient to repeat this desirable brushing action on the inner sides of the lower teeth 70 or of the upper teeth 80 or to brush directly across the crown bases 73 and 83 of the lower and upper teeth, respectively in transverse or longitudinal sweeping operation. The electric motor in the handle 10 is suitably operated on batteries or on conventional 110 volt AC current. A small spotlight may be attached to the side 11' of the housing so that it is collimated to shine directly on the bristles 32 when in the brushing position.

It should be understood that the circularly operated toothbrush cited hereinbefore may be varied as to structure of the toothbrush, the drive means, and the various connection means without departing from the spirit of the invention as disclosed herein, so that it should be understood that the limits of the invention are entirely as defined in the following claims.

What is claimed is:

1. A circularly movable toothbrush comprising:
   A. A handle comprising a housing which is adaptable for manual clasping, having sides and top and bottom and a rotary drive means and power source mounted within said housing, and an externally mounted actuating means for reversibly operating the rotary drive means;
   B. driving means comprising a drive shaft driven by said rotary driving means, a fly wheel connected at its center to said drive shaft, and loosely connected on its opposite side in an off center position to an actuating rod; said actuating rod extending through a head mount portion to a joint portion, and being rotated by said fly wheel in a circular motion to define a circular pattern at and beyond said head mount portion;
   C. said actuating rod being double countersunk at the head mount portion to define a narrow shank portion, a horizontal opening through said narrow shank portion, a guide pin having a diameter of less than said horizontal opening and passing loosely through the opening in said narrow shank portion formed by the double countersink, and said rod rotating at said fly wheel while moving vertically at the portion where the guide pin passes therethrough; and
   D. a toothbrush having a stem which is interchangeably attached to said joint portion, having bristles which remain in alignment with teeth striations and interdental spaces of the teeth when turning in the circular pattern defined by said actuating rod.

2. A toothbrush according to claim 1 wherein a gear train is provided between said fly wheel and said motor to provide control of the speed of said fly wheel and actuating rod.

3. A toothbrush according to claim 2 wherein said actuating rod is connected to said fly wheel by a pin joint near the edge of the fly wheel, said actuating rod being disposed at an angle of 70° to 88° from vertical with respect to the fly wheel.

4. A circularly movable toothbrush comprising:
   A. A handle comprising a housing which is adaptable for manual clasping, having sides and top and bottom and a rotary drove means and power source mounted within said housing, and an externally mounted actuating means for reversibly operating the rotary drive means.
   B. driving means comprising a drive shaft driven by said rotary driving means, a fly wheel connected at its center to said drive shaft, and loosely connected on its opposite side in an off center position to an actuating rod; said actuating rod extending through a head mount portion to a joint portion, and being rotated by said fly wheel in a circular motion to define a circular pattern at and beyond said head mount portion;
   C. said actuating rod being attached by oppositely disposed pins to ring means at the head mount portion, the ring means being in turn attached by a pair of pins to said head mount, said pins providing sufficient up and down motion to permit said actuating rod to revolve therein; and
   D. a toothbrush having a stem which is interchangeably attached to said joint portion, having bristles which remain in alignment with teeth striations and interdental spaces of the teeth when turning in the circular pattern defined by said actuating rod.

5. A toothbrush according to claim 3 wherein a gear train is provided between said fly wheel and said motor to provide control of the speed of said fly wheel and actuating rod.

6. A toothbrush according to claim 5 wherein said actuating rod is connected to said fly wheel by a pin joint near the edge of the fly wheel, said actuating rod being disposed at an angle of 70° to 88° from vertical with respect to the fly wheel.

* * * * *